(12) United States Patent
Liu et al.

(10) Patent No.: US 11,805,814 B2
(45) Date of Patent: Nov. 7, 2023

(54) HIGH EFFICIENCY ATOMIZER AND ELECTRONIC CIGARETTE THEREOF

(71) Applicant: CHINA TOBACCO HUNAN INDUSTRIAL CO., LTD., Hunan (CN)

(72) Inventors: Jianfu Liu, Hunan (CN); Kejun Zhong, Hunan (CN); Xiaoyi Guo, Hunan (CN); Wei Huang, Hunan (CN); Hong Yu, Hunan (CN); Yuangang Dai, Hunan (CN); Xinqiang Yin, Hunan (CN); Jianhua Yi, Hunan (CN); Yongquan Zhou, Hunan (CN); Lizhou Shen, Hunan (CN)

(73) Assignee: CHINA TOBACCO HUNAN INDUSTRIAL CO., LTD., Hunan (CN)

( * ) Notice: Subject to any disclaimer, the term of this patent is extended or adjusted under 35 U.S.C. 154(b) by 1212 days.

(21) Appl. No.: 16/343,641

(22) PCT Filed: Mar. 2, 2017

(86) PCT No.: PCT/CN2017/075454
§ 371 (c)(1),
(2) Date: Apr. 19, 2019

(87) PCT Pub. No.: WO2018/072373
PCT Pub. Date: Apr. 26, 2018

(65) Prior Publication Data
US 2019/0269177 A1    Sep. 5, 2019

(30) Foreign Application Priority Data

Oct. 20, 2016 (CN) .......................... 201621140345.8
Oct. 20, 2016 (CN) .......................... 201621140374.4
Oct. 20, 2016 (CN) .......................... 201621140762.2

(51) Int. Cl.
*A24F 40/00* (2020.01)
*A24F 40/40* (2020.01)
(Continued)

(52) U.S. Cl.
CPC .............. *A24F 40/44* (2020.01); *A24F 40/00* (2020.01); *A24F 40/40* (2020.01); *A24F 40/485* (2020.01);
(Continued)

(58) Field of Classification Search
CPC .......... A24F 40/00; A24F 40/42; A24F 40/40; A24F 40/485
See application file for complete search history.

(56) References Cited

U.S. PATENT DOCUMENTS 5,331,979 A    7/1994 Henley
2020/0214349 A1 *    7/2020 Liu .......................... A24F 40/44
(Continued)

FOREIGN PATENT DOCUMENTS

CN    104382238 A    3/2015
CN    105559151 A    5/2016
(Continued)

OTHER PUBLICATIONS

International Search Report issued in International Application No. PCT/CN2017/075454 dated Jul. 25, 2017, 4 pages.

*Primary Examiner* — Hae Moon Hyeon
(74) *Attorney, Agent, or Firm* — Mauriel Kapouytian Woods LLP; Ran Pang; Michael Mauriel

(57) ABSTRACT

Disclosed is an atomizer, comprising an atomizer body, a suction nozzle assembly mounted at the top of the atomizer body, an air inlet provided in the atomizer body, an atomizing sheet and a tobacco tar cavity provided in the atomizer body, and a tobacco tar guide body which guides tobacco tar in the tobacco tar cavity to an atomizing surface of the
(Continued)

atomizing sheet. The atomizer introduces entered air to allow all the air to pass over, at a low level, the surface where the atomizing cotton is in contact with the atomizing sheet. The atomizing efficiency is higher, and more smoke is produced.

23 Claims, 12 Drawing Sheets

(51) Int. Cl.
  *A24F 40/44* (2020.01)
  *A24F 40/485* (2020.01)
  *A61M 11/04* (2006.01)
  *B05B 7/16* (2006.01)
  *A24F 40/10* (2020.01)

(52) U.S. Cl.
  CPC ............ *A24F 40/10* (2020.01); *A61M 11/042* (2014.02); *B05B 7/1686* (2013.01)

(56) References Cited

U.S. PATENT DOCUMENTS

| | | | |
|---|---|---|---|
| 2021/0076733 A1* | 3/2021 | Liu | ................. B05B 17/0684 |
| 2021/0282456 A1* | 9/2021 | Liu | ..................... A24F 40/10 |
| 2021/0378303 A1* | 12/2021 | Liu | ................. B05B 17/0646 |
| 2022/0151301 A1* | 5/2022 | Liu | ..................... A24F 40/42 |
| 2022/0273037 A1* | 9/2022 | Liu | ..................... A24F 40/42 |

FOREIGN PATENT DOCUMENTS

| | | |
|---|---|---|
| CN | 105795526 A | 7/2016 |
| CN | 205432145 U | 8/2016 |
| CN | 105962421 A | 9/2016 |

* cited by examiner

HIGH EFFICIENCY ATOMIZER AND ELECTRONIC CIGARETTE THEREOF

CROSS REFERENCE TO RELATED APPLICATIONS

This application is a national phase application of international application number PCT/CN2017/075454 filed on Mar. 2, 2017, which claims priority to Chinese application number 201621140762.2 filed on Oct. 20, 2016, Chinese application number 201621140374.4 filed on Oct. 20, 2016, and Chinese application number 201621140345.8 filed on Oct. 20, 2016. The entire contents of these applications are hereby incorporated herein by reference.

FIELD OF THE INVENTION

The present invention belongs to an atomizer and an electronic cigarette thereof.

BACKGROUND OF THE INVENTION

At present, the existing ultrasonic high-frequency atomizing electronic cigarette generally transfers tobacco tar in a tobacco tar cavity to an atomizing sheet through tobacco tar storage cotton, and then atomizes the tobacco tar by high-frequency oscillation through an air inflow passage and an air outflow passage communicated with the atomizing surface of the atomizing sheet. However, the existing product has the following defects in practical application:
1. After air passes through the air inflow passage and flows to the atomizing surface, the entering air is disordered, not all of the air flows to the atomizing surface to participate in atomization, and most of the air directly flows away from the air outflow passage, so that the atomizing efficiency and the amount of smoke are greatly reduced. At the same time, the cold air mixed up with atomized smoke lowers the temperature of the smoke, so that the temperature of the smoke entering the mouth is low and the mouthfeel is poor.
2. The surface of the atomizing sheet is prone to tobacco tar accumulation, especially when the electronic cigarette is not used for a long time. Thus, the tobacco tar continuously penetrates down, which easily causes tobacco tar accumulation. As a result, the tobacco tar is difficult to atomize, and the amount of discharged smoke is small.
3. The heat generated by the atomizing sheet is easily transferred to a shell through the air outflow passage, causing the shell to be very hot.
4. The current air outflow passage is generally a metal pipe. The atomized smoke flows a certain distance in the air outflow passage and then is condensed, which reduces the amount of smoke to a certain extent. In addition, excessively accumulated condensed tobacco tar may be sucked into the mouth to affect the user experience.

SUMMARY OF THE INVENTION

In view of the above problems, the present invention is intended to provide an atomizer having high atomizing efficiency and producing a large amount of smoke, and an electronic cigarette thereof.

The technical solution for solving the problems of the present invention is: an atomizer, comprising an atomizer body, a suction nozzle assembly mounted at the top of the atomizer body, an air inlet provided in the atomizer body, an atomizing sheet and a tobacco tar cavity provided in the atomizer body, and a tobacco tar guide body which guides tobacco tar in the tobacco tar cavity to an atomizing surface of the atomizing sheet, a first air inflow passage which communicates with the air inlet and an air outflow pipe which communicates with the suction nozzle assembly are arranged in the atomizer body, the tobacco tar guide body comprises atomizing cotton which abuts against the atomizing surface of the atomizing sheet, the air outflow pipe is provided with an air guide structure, the lower end of the air guide structure abuts against the atomizing cotton, the air guide structure comprises an air guide passage closely attached to the atomizing cotton, and the air guide passage communicates with the inner cavity of the first air inflow passage as well as the inner cavity of the air outflow pipe.

In the above solution, the air guide passage is designed such that the air entering from the first air inflow passage can be guided to flow, therefore all the air can pass over, at a low level, the surface where the atomizing cotton is in contact with the atomizing sheet, the atomization is more sufficient, the atomizing efficiency is higher, more smoke is produced, the concentration of the obtained smoke is higher, and the mouthfeel of the smoke is improved.

Specifically, the atomizer body further comprises a shell and a connection electrode mounted at the bottom of the shell, the suction nozzle assembly is mounted at the top of the shell, and the atomizing sheet is electrically connected to the connection electrode;

the atomizing cotton is of a hollow cylindrical structure, and the lower part of the air outflow pipe is inserted into the hollow cavity of the atomizing cotton.

In a preferred solution, the air inlet is provided in the lower part of the shell in an area corresponding to the mounting position of the atomizing cotton, and the lower part of the atomizing cotton is provided with a first air pass hole which communicates with the first air inflow passage;

the air guide structure further comprises a base body arranged at the lower part of the air outflow pipe and having a hollow cavity, the base body seals the hollow cavity of the atomizing cotton, the lower end of the base body tightly presses the atomizing cotton with the atomizing sheet from the bottom of the inner cavity of the atomizing cotton, the air guide passage is provided at the lower part of the base body and communicates with the first air pass hole as well as the hollow cavity of the base body, and the hollow cavity of the base body communicates with the air outflow pipe.

Further, the bottom of the tobacco tar cavity is sealed by a first seal seat, a groove is formed in the middle of the first seal seat, and a first tobacco tar isolation seat is mounted in the groove;

the first tobacco tar isolation seat is T-shaped and comprises a first vertical portion and a first flange edge at the top of the first vertical portion, the first vertical portion is inserted into the groove, a first gap is reserved between the first vertical portion and the inner wall of the groove, the first gap is filled with tobacco tar storage cotton, and the first flange edge is provided with a first tobacco tar pass hole, which communicates with the tobacco tar cavity, in a position corresponding to the tobacco tar storage cotton;

the atomizing cotton is wrapped on the outer wall of the first vertical portion, and the outer side of the atomizing cotton abuts against the tobacco tar storage cotton; and the base body is fixedly connected with the first vertical portion.

The air guide passage may have various structures:

In a specific solution, a first seal cover that is open at the bottom is arranged at the lower part of the base body, a second seal cover that is open at the bottom is arranged in the inner cavity of the first seal cover, a gap is reserved between the first seal cover and the second seal cover, and the inner cavity of the second seal cover communicates with the hollow cavity of the base body;

the first seal cover is provided with a first air guide groove in a position corresponding to the first air pass hole, and the second seal cover is provided with a second air guide groove in a position corresponding to the first air guide grooves;

the air guide passage is formed among the first air guide groove, the second air guide groove, and the gap between the first seal cover and the second seal cover;

the first seal cover and the second seal cover abut against the atomizing cotton.

In the above solution, air enters the first air pass hole from the first air inflow passage, then flows through the first air guide groove, the gap between the first seal cover and the second seal cover, and the second air guide groove, and finally flows out from the hollow cavity of the base body. The first air guide groove and the second air guide groove are adjacent to the contact portion of the atomizing cotton and the atomizing sheet to guide the air.

In another specific solution, the hollow cavity of the base body directly reaches the bottom of the base body, a cover which blocks the hollow cavity of the base body is arranged at the bottom of the base body, the cover is provided with a second air pass hole in a position corresponding to the first air pass hole, and the second air pass hole is the air guide passage; the bottom of the cover abuts against the atomizing cotton, and a third air pass hole is formed at the abutting position.

In the above solution, the cover located at the bottom of the hollow cavity of the base body has certain elasticity, thus it has certain deformation space when abutting against the atomizing cotton to improve the contact effect between the atomizing cotton and the atomizing sheet, and at the same time, the second air pass hole has the effect to guide the air.

Preferably, the cover is spherical or inversely conical.

In another preferred solution, the air inlet is provided at the upper part of the shell, an accommodating cavity is formed in the middle of the tobacco tar cavity, the air outflow pipe is arranged in the accommodating cavity, a gap A is reserved between the outer wall of the air outflow pipe and the inner wall of the accommodating cavity, and the gap A communicates with the air inlet to form the first air inflow passage;

a flange is arranged at the lower part of the air outflow pipe near the orifice of the air outflow pipe, the air guide structure comprises a flexible tube sleeved at the orifice of the air outflow pipe below the flange, the lower part of the flexible tube is provided with an air pass groove, and the bottom of the flexible tube abuts against the bottom of the hollow cavity of the atomizing cotton;

after the air outflow pipe is inserted into the hollow cavity of the atomizing cotton, the upper surface of the flange is directly opposite to the outlet of the first air inflow passage; a second gap is reserved between the flange and the outlet of the first air inflow passage, and the side of the flange is close to the inner wall of the hollow cavity of the atomizing cotton, and a third gap is reserved between the flange and the inner wall of the hollow cavity of the atomizing cotton.

In the above solution, the air passage is provided, therefore, after air enters the first air inflow passage, the air is guided to flow through the second gap and the third gap, thereby ensuring that the air can flow along the inner wall of the hollow cavity of the atomizing cotton, thus the smoke generated at the corner of the atomizing cotton can be carried away to avoid the accumulation of smoke and increase the concentration of the smoke. With the air pass groove, air can be guided to flow, and all the air can pass over, at a low level, the surface where the atomizing cotton is in contact with the atomizing sheet, so that the atomization is more sufficient, the atomizing efficiency is higher, and more smoke is produced.

Further, the bottom of the tobacco tar cavity is sealed by a second seal seat, a groove is formed in the middle of the second seal seat, and a second tobacco tar isolation seat is mounted in the groove;

the second tobacco tar isolation seat is T-shaped and comprises a second vertical portion and a second flange edge at the top of the second vertical portion, the second vertical portion is inserted into the groove, a fourth gap is reserved between the second vertical portion and the inner wall of the groove, the fourth gap is filled with tobacco tar storage cotton, and the second flange edge is provided with a second tobacco tar pass hole, which communicates with the tobacco tar cavity, in a position corresponding to the tobacco tar storage cotton;

the side of the atomizing cotton is wrapped on the outer wall of the second vertical portion, and the side of the atomizing cotton abuts against the tobacco tar storage cotton.

The bottom of the atomizing cotton is provided with a first air outlet.

In order to ensure closer contact between the atomizing cotton and the atomizing sheet, the lower part of the second vertical portion is sleeved with a spring, the spring is wrapped by the atomizing cotton, the lower end of the spring abuts against the inner surface of the bottom of the atomizing cotton, the lower part of the air outflow pipe penetrates through the second tobacco tar isolation seat and is inserted into a central hole of the spring, and the flexible tube communicates with the first air outlet.

Further, the flexible tube is a glass fiber tube, and comprises a first glass fiber tube sleeved at the lower part of the air outflow pipe and a second glass fiber tube sleeved at the upper part of the outer wall of the first glass fiber tube;

the length of the second glass fiber tube is shorter than that of the first glass fiber tube, and the air pass groove is formed at the lower part edge of the first glass fiber tube.

The second glass fiber tube mainly improves the strength of the first glass fiber tube to prevent bending during assembly.

Further, a filter screen is arranged at the lower part of the inner cavity of the air outflow pipe. The filter screen is used for blocking tobacco tar from splashing or large particle smoke from being sucked into the user's mouth when the atomizing sheet is operated.

In another preferred solution, the air inlet is provided at the upper part of the shell, a tobacco tar isolation cavity is formed in the middle of the tobacco tar cavity, an accommodating cavity is formed in the tobacco tar isolation cavity, the air outflow pipe is arranged in the accommodating cavity, a gap B is reserved between the outer wall of the air outflow pipe and the inner wall of the accommodating cavity, and the gap B communicates with the air inlet to form the first air inflow passage;

the air guide structure comprises a liner tube which is sleeved in the inner cavity of the air outflow pipe and has the performance of thermal insulation and tobacco tar absorption, a gap C is reserved between the lower end of the air outflow pipe and the bottom of the hollow cavity of the atomizing cotton, the lower end of the liner tube stretches out of the lower end of the air outflow pipe and abuts against the bottom of the hollow cavity of the atomizing cotton, the lower part edge of the liner tube is provided with an air pass hole F which communicates with the first air inflow passage, and the air pass hole F is the air guide passage.

In the above solution, the air pass hole F is designed such that the air can be guided to flow, thus all the air can pass over, at a low level, the surface where the atomizing cotton is in contact with the atomizing sheet, the atomization is more sufficient, the atomizing efficiency is higher, and more smoke is produced.

The liner tube itself has the thermal insulation function, and the lower end of the air pipe is not in contact with the atomizing cotton, so that the heat produced by the atomizing sheet can be prevented from being transferred to the shell through the air pipe.

In addition, the liner tube has the performance of tobacco tar absorption. When the smoke flows to the upper part of the air pipe and is condensed, the condensed smoke can adsorb the condensed tobacco tar, and is guided again to the atomizing cotton from top to bottom for secondary atomizing to prevent the condensed tobacco tar from being sucked into the mouth to affect the mouthfeel.

Further, the height of the air pass hole F is 0.2 to 0.7 mm. The reserved air pass hole is small, thus air can be guided to flow, and all the air can pass over, at a low level, the surface where the atomizing cotton is in contact with the atomizing sheet, so that the atomization is more sufficient.

Specifically, the accommodating cavity is composed of an outer sleeve and an inner sleeve sleeved in the inner cavity of the outer sleeve, the outer sleeve comprises a hollow third seal seat arranged at the bottom of the tobacco tar cavity to seal the tobacco tar cavity and a vertical pipe fixed on the third seal seat, the inner sleeve is sleeved in the inner cavity of the vertical pipe, and the inner cavity of the inner sleeve is the accommodating cavity; an atomizing sheet fixing holder is arranged in the hollow cavity of the third seal seat, and the atomizing sheet is fixed on the atomizing sheet fixing holder;

the side wall of the atomizing cotton is sandwiched and fixed between the outer wall of the inner sleeve and the inner wall of the vertical pipe; the lower part of the vertical pipe is provided with a plurality of third tobacco tar pass holes in positions corresponding to the side wall of the atomizing cotton, and the third tobacco tar pass holes communicate with the tobacco tar cavity;

the air outflow pipe with the liner tube is inserted into the hollow cavity of the inner sleeve as well as the hollow cavity of the atomizing cotton.

Further, tobacco tar storage cotton is sleeved on the outer wall of the vertical pipe at a position corresponding to the third tobacco tar pass holes, and the tobacco tar storage cotton is located in the tobacco tar cavity and covers the third tobacco tar pass holes. The tobacco tar storage cotton can control the tobacco tar transfer rate and prevent the atomizing cotton from absorbing too much tobacco tar to produce tobacco tar accumulation.

In order to ensure closer contact between the atomizing cotton and the atomizing sheet, the lower part of the inner cavity of the inner sleeve is sleeved with a spring, the lower end of the spring abuts against the inner surface of the bottom of the atomizing cotton, and the air outflow pipe with the liner tube is inserted into the hollow cavity of the inner sleeve as well as the central hole of the spring.

Further, the air outflow pipe is flush with the upper end of the liner tube, and a filter screen is arranged at the upper part of the liner tube. The filter screen is used for blocking tobacco tar from splashing or large particle smoke from being sucked into the user's mouth when the atomizing sheet is operated.

Further, the liner tube is a glass fiber tube, and the air pass hole F is zigzag groove or wave groove formed around the lower part edge of the liner tube.

For better thermal insulation, the height of the gap C between the air outflow pipe and the bottom of the hollow cavity of the atomizing cotton is more than 2 mm. The lower end of the air outflow pipe is not in contact with the atomizing cotton, which can prevent the heat produced by the atomizing sheet from being transferred to the shell through the air outflow pipe.

In an improved solution, the upper end of the liner tube extends out of the upper end of the air outflow pipe and extends into the inner cavity of the suction nozzle assembly, and a gap D is reserved between the outer wall of the liner tube and the inner cavity wall of the suction nozzle assembly;

the suction nozzle assembly is detachably connected to the top of the shell.

The liner tube is directly extended up to a suction nozzle, and the suction nozzle is made of other non-metallic material such as plastic or wood, so that the entire air outflow passage can greatly reduce the occurrence of condensation. The gap D is provided to facilitate the disassembly and assembly of the suction nozzle.

Further, a thermal insulation sheet is arranged between the lower surface of the atomizing sheet and the connection electrode. The thermal insulation sheet can prevent the heat of the atomizing sheet from being transferred from the lower part to the connection electrode and the shell.

Preferably, the atomizing sheet is a solid piezoelectric ceramic sheet.

Correspondingly, the present invention also provides an electronic cigarette, comprising an external power source, and the atomizer according to the above solution, wherein the external power source is connected to the connection electrode of the atomizer.

By adding the air guide passage on the basis of the prior art, the incoming air can be correctly guided to flow, so that all the air can pass over, at a low level, the surface where the atomizing cotton is in contact with the atomizing sheet, the atomization is more sufficient, the atomizing efficiency is higher, and more smoke is produced. Moreover, cold air is prevented from flowing away directly from the air pipe to be mixed with the smoke to reduce the temperature of the smoke, thereby avoiding the phenomenon that the low temperature of the smoke affects the mouthfeel.

BRIEF DESCRIPTION OF THE DRAWINGS

The present invention will be further illustrated below in conjunction with the accompanying drawings.

Figure 1:
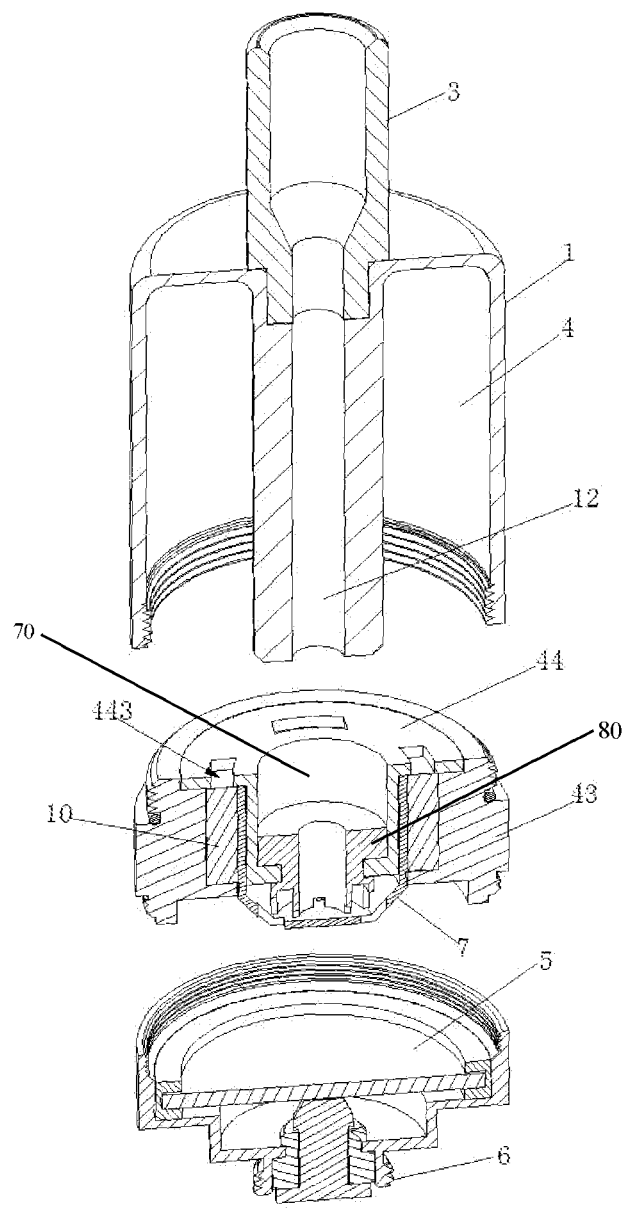
FIG. 1 is an oblique exploded view of an atomizer in Embodiment 1.
Figure 2:
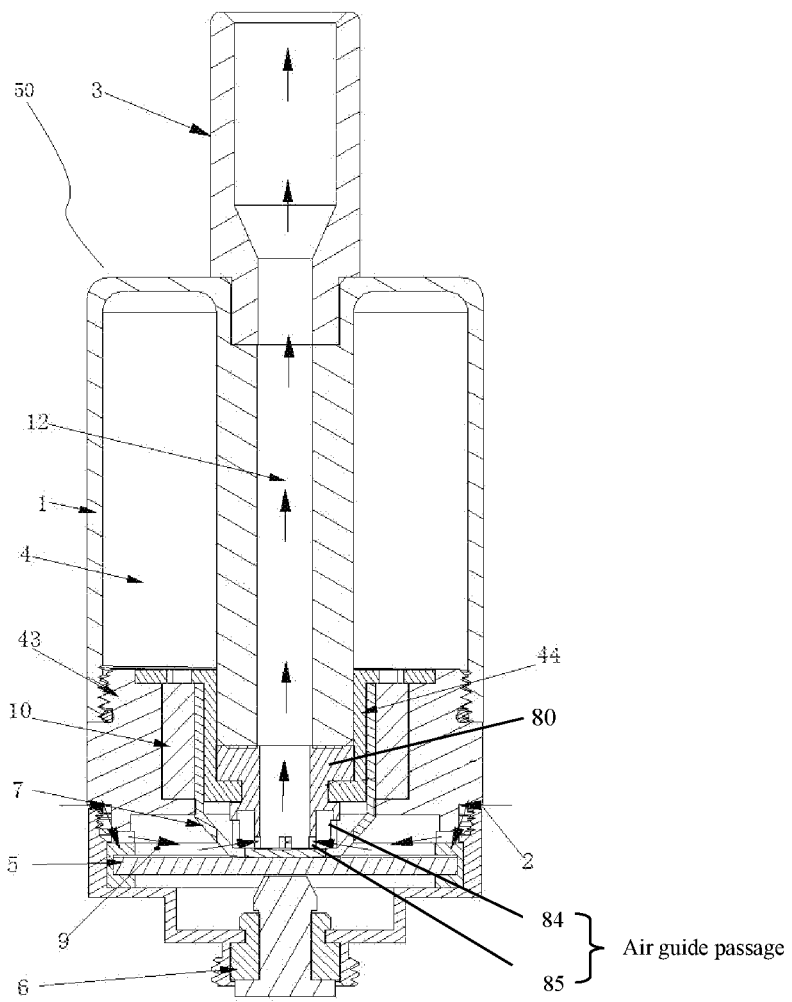
FIG. 2 is a sectional view of Embodiment 1.
Figure 3:
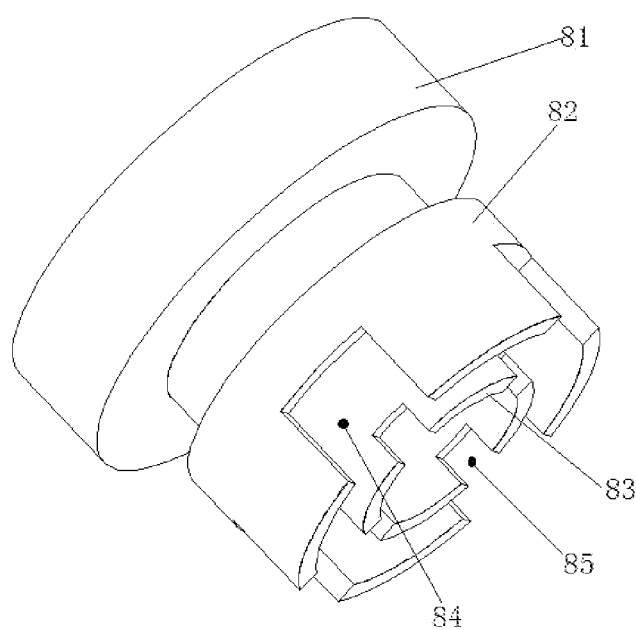
FIG. 3 is a schematic view of an air guide structure in Embodiment 1.
Figure 4:
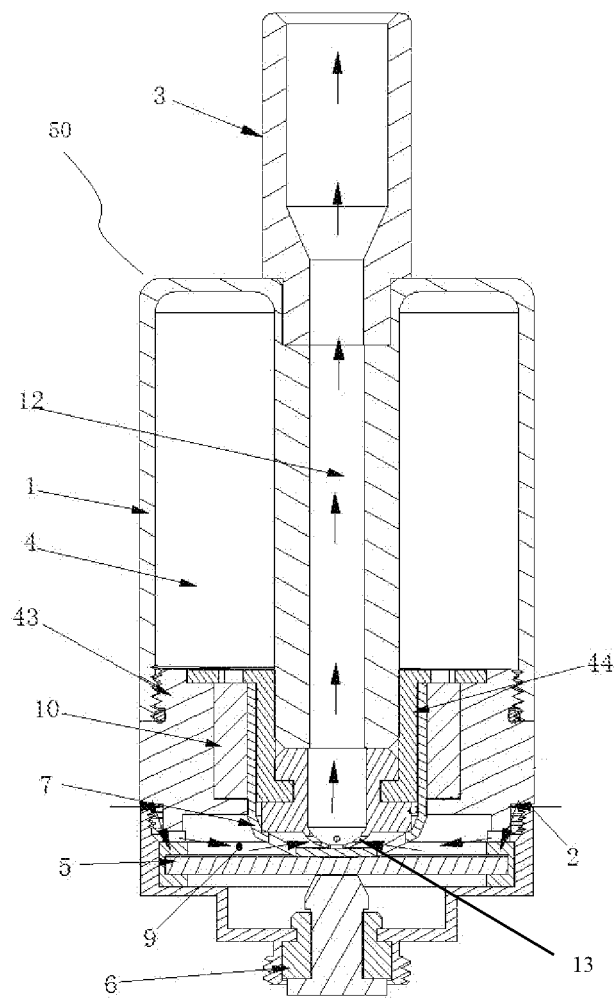
FIG. 4 is a sectional view of Embodiment 2.
Figure 5:
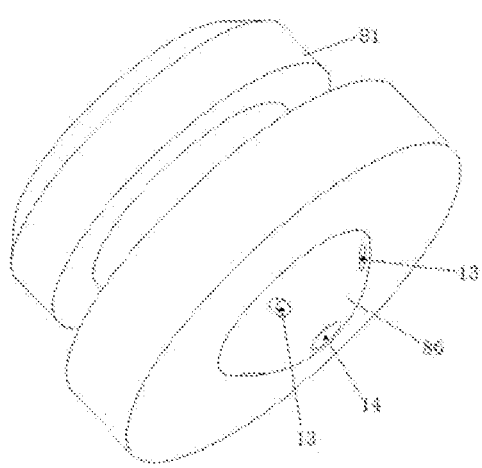
FIG. 5 is a schematic view of an air guide structure in Embodiment 2.
Figure 6:
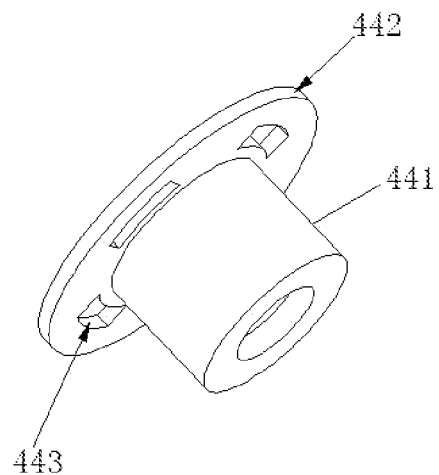
FIG. 6 is a structural view of a first tobacco tar isolation seat in Embodiments 1 and 2.
Figure 7:
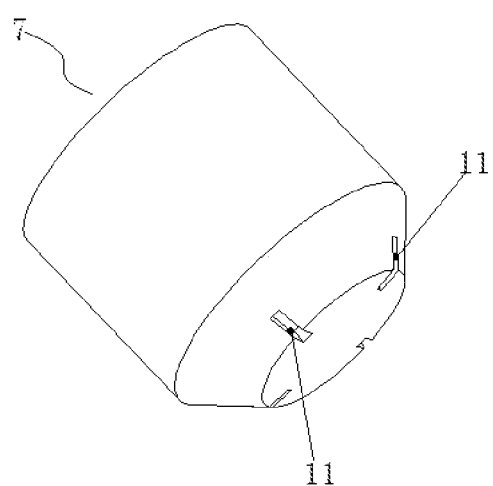
FIG. 7 is a structural view of atomizing cotton in Embodiments 1 and 2.
Figure 8:
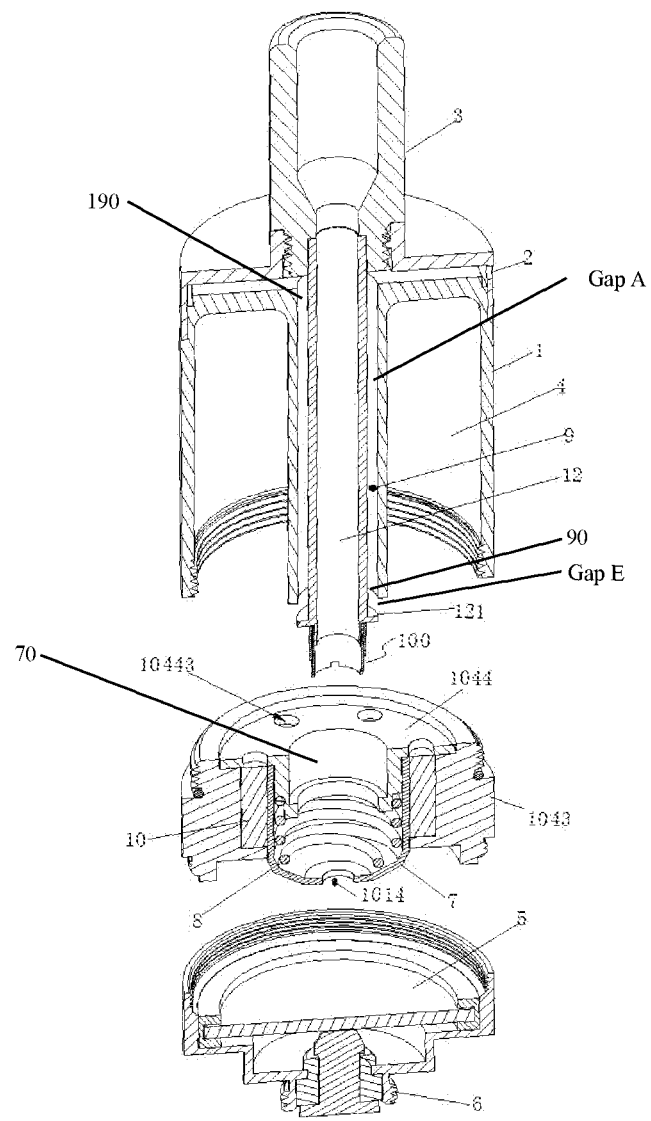
FIG. 8 is an oblique exploded view of an atomizer in Embodiment 3.
Figure 9:
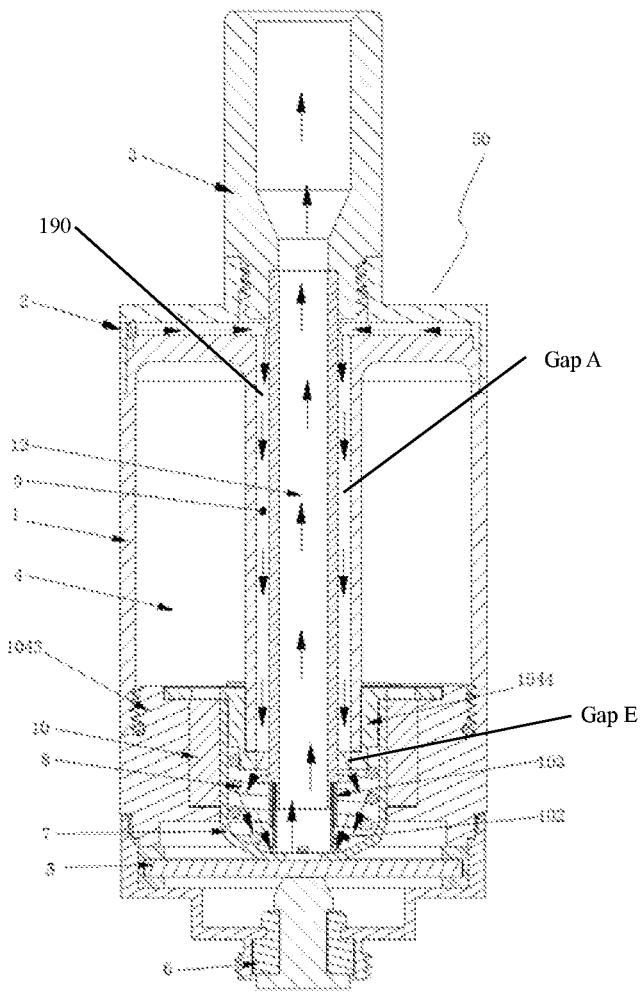
FIG. 9 is a sectional view of Embodiment 3.
Figure 10:
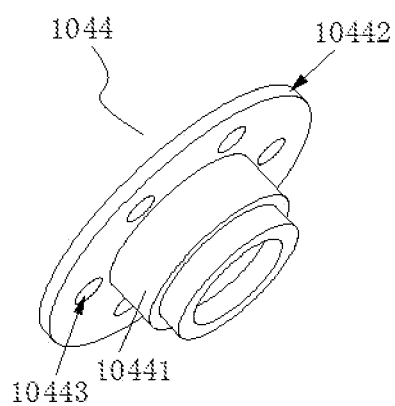
FIG. 10 is a structural view of a second tobacco tar isolation seat in Embodiment 3.
Figure 11:
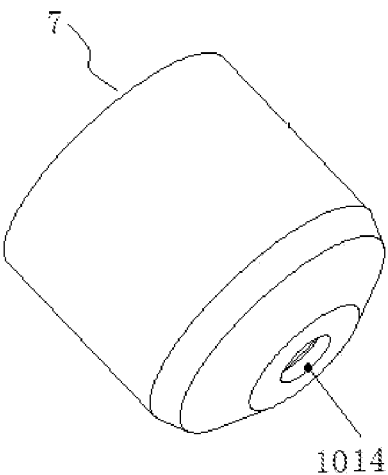
FIG. 11 is a structural view of atomizing cotton in Embodiment 3.
Figure 12:
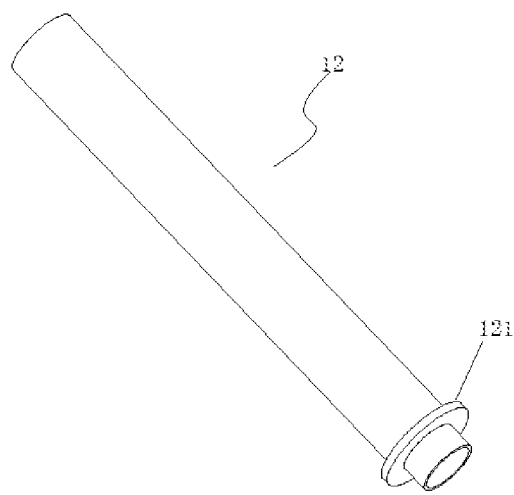
FIG. 12 is a structural view of an air outflow pipe in Embodiment 3.
Figure 13:
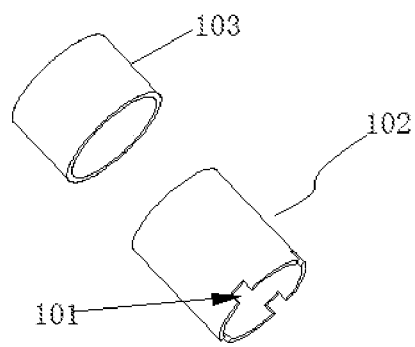
FIG. 13 is a structural exploded view of a flexible tube in Embodiment 3.

In the figures: 1—shell, 2—air inlet, 3—suction nozzle assembly, 4—tobacco tar cavity, 5—atomizing sheet, 6—connection electrode, 7—atomizing cotton, 8—spring, 9—first air inflow passage, 10—tobacco tar storage cotton, 11—first air pass hole, 12—air outflow pipe, 13—second air pass hole, 14—third air pass hole, 15—filter screen, 16—inner sleeve, 17—thermal insulation sheet, 18—atomizing sheet fixing holder, 19—tobacco tar isolation cavity, 20—air pass hole F, 43—first seal seat, 44—first tobacco tar isolation seat, 50—atomizer body, 70—hollow cavity of the atomizing cotton, 80—air guide structure, 81—base body, 82—first seal cover, 83—second seal cover, 84—first air guide groove, 85—second air guide groove, 86—cover, 90—outlet of the first air inflow passage, 100—flexible tube, 101—air pass groove, 102—first glass fiber tube, 103—second glass fiber tube, 111—third seal seat, 112—vertical pipe, 113—third tobacco tar pass hole, 121—flange, 190—accommodating cavity, 441—first vertical portion, 442—first flange edge, 443—first tobacco tar pass hole, 1010—liner tube, 1011—outer sleeve, 1014—first air outlet, 1043—second seal seat, 1044—second tobacco tar isolation seat, 10441—second vertical portion, 10442—second flange edge, 10443—second tobacco tar pass hole.

DETAILED DESCRIPTION OF THE EMBODIMENTS

Embodiment 1

As shown in FIGS. 1-3, 6 and 7, an atomizer includes an atomizer body 50, a suction nozzle assembly 3 mounted at the top of the atomizer body 50, an air inlet 2 provided in the atomizer body 50, an atomizing sheet 5 and a tobacco tar cavity 4 provided in the atomizer body 50, and a tobacco tar guide body which guides tobacco tar in the tobacco tar cavity 4 to an atomizing surface of the atomizing sheet 5. A first air inflow passage 9 which communicates with the air inlet 2 and an air outflow pipe 12 which communicates with the suction nozzle assembly 3 are arranged in the atomizer body 50. The tobacco tar guide body includes atomizing cotton 7 which abuts against the atomizing surface of the atomizing sheet 5. The air outflow pipe 12 is provided with an air guide structure 80, and the lower end of the air guide structure 80 abuts against the atomizing cotton 7. The air guide structure 80 includes an air guide passage closely attached to the atomizing cotton 7, and the air guide passage communicates with the inner cavity of the first air inflow passage 9 as well as the inner cavity of the air outflow pipe 12.

The atomizer body 50 further includes a shell 1 and a connection electrode 6 mounted at the bottom of the shell 1, the suction nozzle assembly 3 is mounted at the top of the shell 1, and the atomizing sheet 5 is electrically connected to the connection electrode 6.

The atomizing cotton 7 is of a hollow cylindrical structure, and the lower part of the air outflow pipe 12 is inserted into the hollow cavity 70 of the atomizing cotton 7.

The air inlet is provided in the lower part of the shell 1 in an area corresponding to the mounting position of the atomizing cotton 7, and the lower part of the atomizing cotton 7 is provided with a first air pass hole 11 which communicate with the first air inflow passage 9.

The air guide structure 80 further includes a base body 81 arranged at the lower part of the air outflow pipe 12 and having a hollow cavity. The base body 81 blocks the hollow cavity 70 of the atomizing cotton 7, and the lower end of the base body 81 tightly presses the atomizing cotton 7 with the atomizing sheet 5 from the bottom of the inner cavity of the atomizing cotton 7. The air guide passage is provided at the lower part of the base body 81 and communicates with the first air pass hole 11 as well as the hollow cavity of the base body 81, and the hollow cavity of the base body 81 communicates with the air outflow pipe 12.

The bottom of the tobacco tar cavity 4 is sealed by a first seal seat 43, a groove is formed in the middle of the first seal seat 43, and a first tobacco tar isolation seat 44 is mounted in the groove. The first tobacco tar isolation seat 44 is T-shaped, and includes a first vertical portion 441 and a first flange edge 442 at the top of the first vertical portion 441. The first vertical portion 441 is inserted into the groove, a first gap is reserved between the first vertical portion 441 and the inner wall of the groove, the first gap is filled with tobacco tar storage cotton 10, and the first flange edge 442 is provided with a first tobacco tar pass hole 443, which communicates with the tobacco tar cavity 4, in a position corresponding to the tobacco tar storage cotton 10. The atomizing cotton 7 is wrapped on the outer wall of the first vertical portion 441, and the outer side of the atomizing cotton 7 abuts against the tobacco tar storage cotton 10. The base body 81 is fixedly connected to the first vertical portion 441.

A first seal cover 82 that is open at the bottom is arranged at the lower part of the base body 81. A second seal cover 83 that is open at the bottom is arranged in the inner cavity of the first seal cover 82. A gap is reserved between the first seal cover 82 and the second seal cover 83, and the inner cavity of the second seal cover 83 communicates with the hollow cavity of the base body 81. The first seal cover 82 is provided with a first air guide grooves 84 in a position corresponding to the first air pass hole 11, and the second seal cover 83 is provided with second air guide grooves 85 in a position corresponding to the first air guide grooves 84. The air guide passage (84 and 85) is formed among the first air guide groove 84, the second air guide groove 85, and the gap between the first seal cover 82 and the second seal cover 83. The first seal cover 82 and the second seal cover 83 abut against the atomizing cotton 7. The present embodiment further provides an electronic cigarette, including an external power source, and further including an atomizer according to the above solution, wherein the external power source is connected to the connection electrode 6 of the atomizer.

Embodiment 2

As shown in FIGS. 4-7, the contents of Embodiment 1 is repeated, except that the structure of the air guide passage is different. The hollow cavity of the base body 81 directly reaches the bottom of the base body 81, a spherical or inversely conical cover 86 which blocks the hollow cavity of the base body 81 is arranged at the bottom of the base body 81, the cover 86 is provided with a second air pass hole 13 in a position corresponding to the first air pass hole 11, and the second air pass hole 13 is the air guide passage.

The bottom of the cover 86 abuts against the atomizing cotton 7, and a third air pass hole 14 is formed at the abutting position.

Embodiment 3

As shown in FIGS. 8-13, an atomizer includes an atomizer body 50, a suction nozzle assembly 3 mounted at the top of the atomizer body 50, an air inlet 2 provided in the atomizer body 50, an atomizing sheet 5 and a tobacco tar cavity 4 provided in the atomizer body 50, and a tobacco tar guide body which guides tobacco tar in the tobacco tar cavity 4 to an atomizing surface of the atomizing sheet 5. A first air inflow passage 9 which communicates with the air inlet 2 and an air outflow pipe 12 which communicates with the suction nozzle assembly 3 are arranged in the atomizer body 50. The tobacco tar guide body includes atomizing cotton 7 which abuts against the atomizing surface of the atomizing sheet 5. The air outflow pipe 12 is provided with an air guide structure, and the lower end of the air guide structure abuts against the atomizing cotton 7. The air guide structure includes an air guide passage closely attached to the atomizing cotton 7, and the air guide passage communicates with the inner cavity of the first air inflow passage 9 as well as the inner cavity of the air outflow pipe 12.

The atomizer body 50 further includes a shell 1 and a connection electrode 6 mounted at the bottom of the shell 1, the suction nozzle assembly 3 is mounted at the top of the shell 1, and the atomizing sheet 5 is electrically connected to the connection electrode 6. The atomizing sheet 5 is preferably a solid piezoelectric ceramic sheet.

The atomizing cotton 7 is of a hollow cylindrical structure, and the lower part of the air outflow pipe 12 is inserted into the hollow cavity 70 of the atomizing cotton 7. A first air outlet 1014 is formed at the bottom of the atomizing cotton 7.

The air inlet 2 is provided at the upper part of the shell 1, and an accommodating cavity 190 is formed in the middle of the tobacco tar cavity 4. The air outflow pipe 12 is arranged in the accommodating cavity 190, a gap A is reserved between the outer wall of the air outflow pipe 12 and the inner wall of the accommodating cavity 190, and the gap A communicates with the air inlet 2 to form the first air inflow passage 9.

A flange 121 is arranged at the lower part of the air outflow pipe 12 near the orifice of the air outflow pipe 12. The air guide structure comprises a flexible tube 100 sleeved at the orifice of the air outflow pipe 12 below the flange 121, and the lower part of the flexible tube 100 is provided with an air pass groove 101. The bottom of the flexible tube 100 abuts against the bottom of the hollow cavity 70 of the atomizing cotton 7. The flexible tube 100 is a glass fiber tube, and comprises a first glass fiber tube 102 sleeved at the lower part of the air outflow pipe 12 and a second glass fiber tube 103 sleeved at the upper part of the outer wall of the first glass fiber tube 102. The length of the second glass fiber tube 103 is shorter than that of the first glass fiber tube 102, and the air pass groove 101 is formed at the lower part edge of the first glass fiber tube 102.

After the air outflow pipe 12 is inserted into the hollow cavity 70 of the atomizing cotton 7, the upper surface of the flange 121 is directly opposite to the outlet 90 of the first air inflow passage 9, and a second gap (E) is reserved between the flange 121 and the outlet 90 of the first air inflow passage 9. The side of the flange 121 is close to the inner wall of the hollow cavity 70 of the atomizing cotton 7, and a third gap is reserved between the flange 121 and the inner wall of the hollow cavity 70 of the atomizing cotton 7.

The bottom of the tobacco tar cavity 4 is sealed by a second seal seat 1043, a groove is formed in the middle of the second seal seat 1043, and a second tobacco tar isolation seat 1044 is mounted in the groove. The second tobacco tar isolation seat 1044 is T-shaped and includes a second vertical portion 10441 and a second flange edge 10442 at the top of the second vertical portion 10441, the second vertical portion 10441 is inserted into the groove, a fourth gap is reserved between the second vertical portion 10441 and the inner wall of the groove, the fourth gap is filled with tobacco tar storage cotton 10, and the second flange edge 10442 is provided with a second tobacco tar pass hole 10443, which communicates with the tobacco tar cavity 4, in a position corresponding to the tobacco tar storage cotton 10. The side of the atomizing cotton 7 is wrapped on the outer wall of the second vertical portion 10441, and the side of the atomizing cotton 7 abuts against the tobacco tar storage cotton 10.

The lower part of the second vertical portion 10441 is sleeved with a spring 8. The spring 8 is wrapped by the atomizing cotton 7, and and the lower end of the spring 8 abuts against the inner surface of the bottom of the atomizing cotton 7. The lower part of the air outflow pipe 12 penetrates through the second tobacco tar isolation seat 1044 and is inserted into the central hole of the spring 8, and the flexible tube 100 communicates with the first air outlet 1014.

The present embodiment further provides an electronic cigarette, including an external power source, and further including an atomizer according to the above solution, wherein the external power source is connected to the connection electrode 6 of the atomizer.

When the electronic cigarette is in operation, after the air enters the first air inflow passage 9, the air is guided to flow through the second gap (E) and the third gap, flows along the inner wall of the hollow cavity 70 of the atomizing cotton 7, and then carries away the smoke generated at corners of the atomizing cotton 7 to avoid accumulation of the smoke. Then, the air flows through the air pass groove 101 and is guided to flow, so that all the air can pass over, at a low level, the surface where the atomizing cotton 7 is in contact with the atomizing sheet 5, the atomization is more sufficient, the atomizing efficiency is higher, and more smoke is produced.

Embodiment 4

Figure 14:
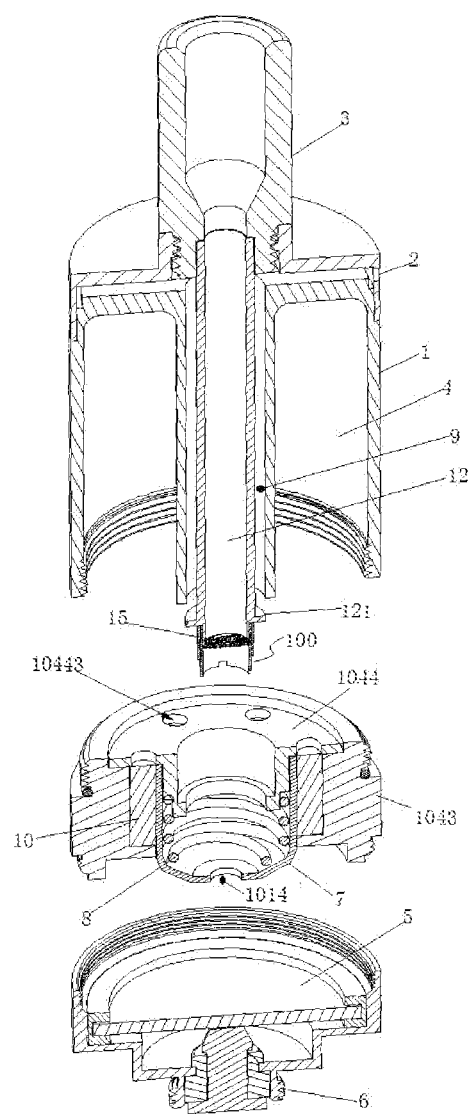
FIG. 14 is an oblique exploded view of an atomizer in Embodiment 4.
Figure 15:
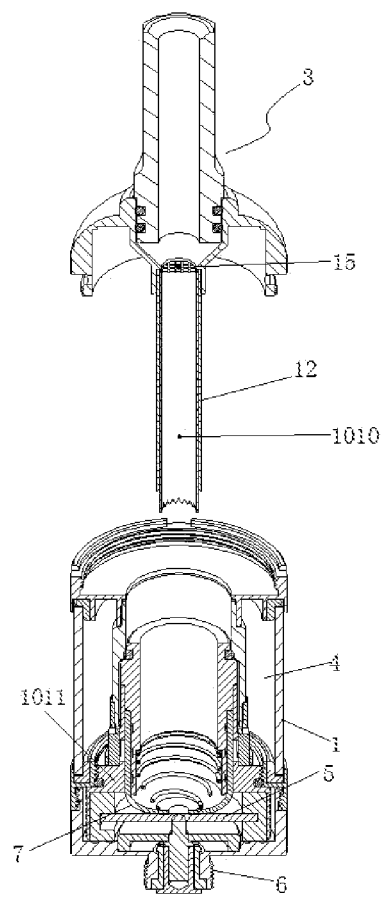
FIG. 15 is an oblique exploded view of an atomizer in Embodiment 5.
Figure 16:
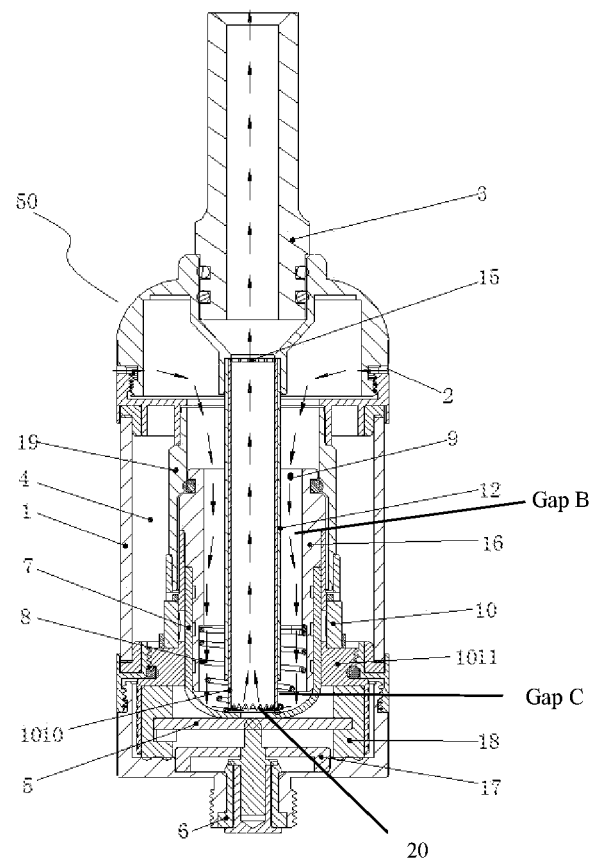
FIG. 16 is a sectional view of Embodiment 5.
Figure 17:
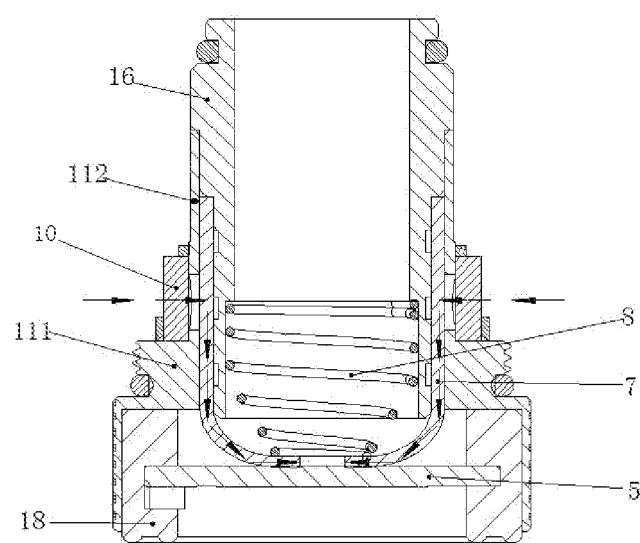
FIG. 17 is a view of an assembly structure of an outer sleeve and an inner sleeve in Embodiment 5.
Figure 18:
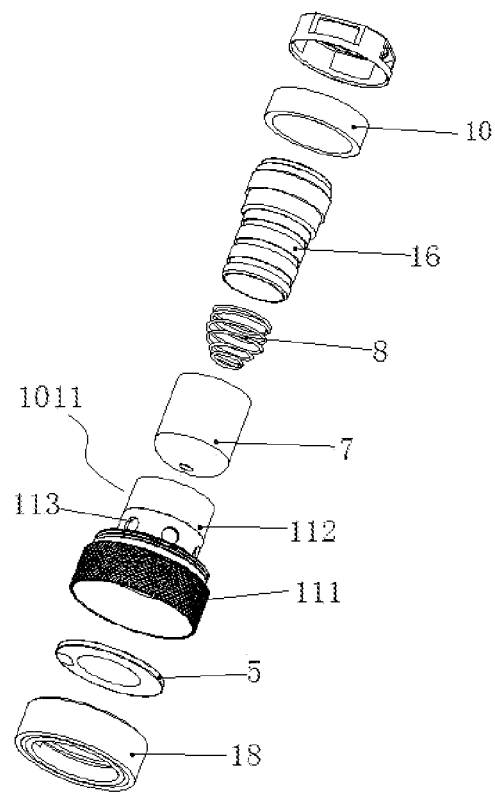
FIG. 18 is an exploded view of the assembly structure of the outer sleeve and the inner sleeve in Embodiment 5.
Figure 19:
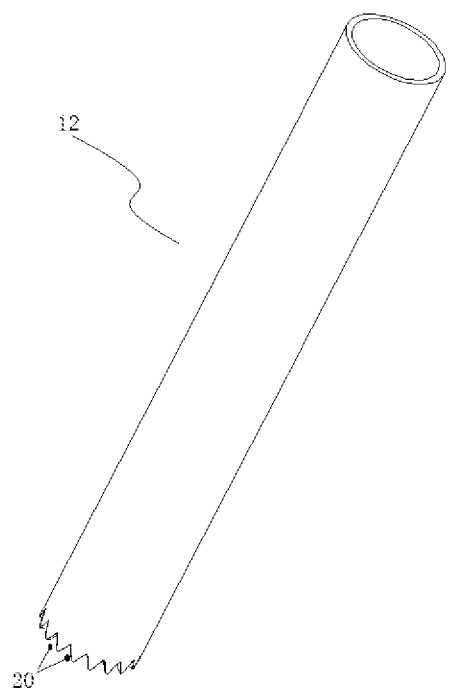
FIG. 19 is a structural view of a liner tube in Embodiment 5.

As shown in FIG. 14, the contents of Embodiment 3 is repeated, except that a filter screen 15 is arranged at the lower part of the inner cavity of the air outflow pipe 12, and the filter screen 15 is used for blocking tobacco tar from splashing or large particle smoke from being sucked into the user's mouth when the atomizing sheet 5 is in operation.

Embodiment 5

As shown in FIGS. 15-19, an atomizer, including an atomizer body 50, a suction nozzle assembly 3 mounted at the top of the atomizer body 50, an air inlet 2 provided in the atomizer body 50, an atomizing sheet 5 and a tobacco tar cavity 4 provided in the atomizer body 50, and a tobacco tar guide body which guides tobacco tar in the tobacco tar cavity 4 to an atomizing surface of the atomizing sheet 5. A first air inflow passage 9 which communicates with the air inlet 2 and an air outflow pipe 12 which communicates with the suction nozzle assembly 3 are arranged in the atomizer body 50. The tobacco tar guide body includes atomizing cotton 7 which abuts against the atomizing surface of the atomizing sheet 5. The air outflow pipe 12 is provided with an air guide structure, and the lower end of the air guide structure abuts against the atomizing cotton 7. The air guide structure includes an air guide passage closely attached to the atomizing cotton 7, and the air guide passage communicates with the inner cavity of the first air inflow passage 9 as well as the inner cavity of the air outflow pipe 12.

The atomizer body 50 further includes a shell 1 and a connection electrode 6 mounted at the bottom of the shell 1, the suction nozzle assembly 3 is mounted at the top of the shell 1, and the atomizing sheet 5 is electrically connected to the connection electrode 6. A thermal insulation sheet 17 is arranged between the lower surface of the atomizing sheet 5 and the connection electrode 6. The atomizing sheet 5 is preferably a solid piezoelectric ceramic sheet.

The atomizing cotton 7 is of a hollow cylindrical structure, and the lower part of the air outflow pipe 12 is inserted into the hollow cavity of the atomizing cotton 7.

The air inlet 2 is provided at the upper part of the shell 1, and a tobacco tar isolation cavity 19 is formed in the middle of the tobacco tar cavity 4. An accommodating cavity 190 is formed in the tobacco tar isolation cavity 19. The air outflow pipe 12 is arranged in the accommodating cavity 190, a gap B is reserved between the outer wall of the air outflow pipe 12 and the inner wall of the accommodating cavity 190, and the gap B communicates with the air inlet 2 to form the first air inflow passage 9.

The accommodating cavity 190 is composed of an outer sleeve 1011 and an inner sleeve 16 sleeved in the inner cavity of the outer sleeve 1011. The outer sleeve 1011 includes a hollow third seal seat 111 arranged at the bottom of the tobacco tar cavity 4 to seal the tobacco tar cavity 4, and a vertical pipe 112 fixed on the third seal seat 111. The inner sleeve 16 is sleeved in the inner cavity of the vertical pipe 112, and the inner cavity of the inner sleeve 16 is the accommodating cavity 190. An atomizing sheet fixing holder 18 is arranged in the hollow cavity of the third seal seat 111, and the atomizing sheet 5 is fixed on the atomizing sheet fixing holder 18. The side wall of the atomizing cotton 7 is sandwiched and fixed between the outer wall of the inner sleeve 16 and the inner wall of the vertical pipe 112. The lower part of the vertical pipe 112 is provided with a plurality of third tobacco tar pass holes 113 in positions corresponding to the side wall of the atomizing cotton 7, and the third tobacco tar pass holes 113 communicate with the tobacco tar cavity 4. Tobacco tar storage cotton 10 is sleeved on the outer wall of the vertical pipe 112 at a position corresponding to the third tobacco tar pass holes 113, and the tobacco tar storage cotton 10 is located in the tobacco tar cavity 4 and covers the third tobacco tar pass holes 113. The lower part of the inner cavity of the inner sleeve 16 is sleeved with a spring 8, and the lower end of the spring 8 abuts against the inner surface of the bottom of the atomizing cotton 7.

The air guide structure comprises a liner tube 1010 which is sleeved in the inner cavity of the air outflow pipe 12 and has the performance of thermal insulation and tobacco tar absorption. The liner tube 1010 is a glass fiber tube, and the air pass hole F 20 is zigzag groove formed around the lower part edge of the liner tube 1010.

A gap C is reserved between the lower end of the air outflow pipe 12 and the bottom of the hollow cavity of the atomizing cotton 7. The height of the gap C is more than 2 mm. The lower end of the liner tube 1010 extends out of the lower end of the air outflow pipe 12 and abuts against the bottom of the hollow cavity of the atomizing cotton 7, and the lower part edge of the liner tube 1010 is provided with an air pass hole F 20 which communicates with the first air inflow passage 9. The air pass hole F is the air guide passage. The height of the air pass hole F 20 is 0.2 to 0.7 mm.

The air out pipe 12 with the liner tube 1010 is inserted into the hollow cavity of the inner sleeve 16 as well as the central hole of the spring 8.

The air outflow pipe 12 is flush with the upper end of the liner tube 1010, and a filter screen 15 is arranged at the upper part of the liner tube 1010.

The present embodiment further provides an electronic cigarette, including an external power source, and further including an atomizer according to the above solution, wherein the external power source is connected to the connection electrode 6 of the atomizer.

Air enters from the air inlet 2, flows through the first air inflow passage 9, and arrives at the atomizing surface from the air pass hole F20. The atomized smoke arrives at the suction nozzle assembly 3 from the liner tube 1010.

Embodiment 6

Figure 20:
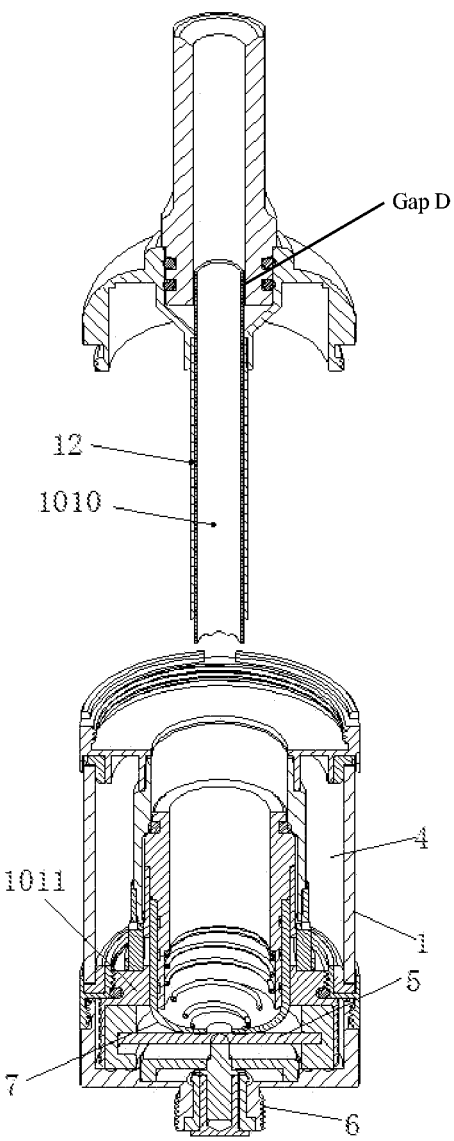
FIG. 20 is an oblique exploded view of an atomizer in Embodiment 6.

As shown in FIG. 20, the contents of Embodiment 5 are repeated, except that the air pass hole F20 is wave groove. The upper end of the liner tube 1010 extends out of the upper end of the air outflow pipe 12 and extends into the inner cavity of the suction nozzle assembly 3, and a gap D is reserved between the outer wall of the liner tube 1010 and the inner cavity wall of the suction nozzle assembly 3. The suction nozzle assembly 3 is detachably connected to the top of the shell 1.

The invention claimed is:

1. An atomizer, comprising an atomizer body, a suction nozzle assembly mounted at a top of the atomizer body, an air inlet provided in the atomizer body, an atomizing sheet and a tobacco tar cavity provided in the atomizer body, and a tobacco tar guide body which guides tobacco tar in the tobacco tar cavity to an atomizing surface of the atomizing sheet, wherein a first air inflow passage which communicates with the air inlet and an air outflow pipe which communicates with the suction nozzle assembly are arranged in the atomizer body, wherein the tobacco tar guide body comprises atomizing cotton which abuts against the atomizing surface of the atomizing sheet, wherein the air outflow pipe is provided with an air guide structure, a lower end of the air guide structure abuts against the atomizing cotton, wherein the air guide structure comprises an air guide passage closely attached to the atomizing cotton, and wherein the air guide passage communicates with the first air inflow passage as well as the air outflow pipe.

2. The atomizer according to claim 1, wherein the atomizer body further comprises a shell and a connection electrode mounted at a bottom of the shell, the suction nozzle assembly is mounted at a top of the shell, and the atomizing sheet is electrically connected to the connection electrode;

wherein the atomizing cotton is of a hollow cylindrical structure with a hollow cavity, and a lower part of the air outflow pipe is inserted into the hollow cavity of the atomizing cotton.

3. The atomizer according to claim 2, wherein the air inlet is provided in a lower part of the shell in an area corresponding to the mounting position of the atomizing cotton, and a lower part of the atomizing cotton is provided with a first air pass hole which communicates with the first air inflow passage;

wherein the air guide structure further comprises a base body arranged at the lower part of the air outflow pipe and having a hollow cavity, the base body seals the hollow cavity of the atomizing cotton, a lower end of the base body tightly presses the atomizing cotton with the atomizing sheet from a bottom of an inner cavity of the atomizing cotton, the air guide passage is provided at a lower part of the base body and communicates with the first air pass hole as well as the hollow cavity of the base body, and the hollow cavity of the base body communicates with the air outflow pipe.

4. The atomizer according to claim 3, wherein a bottom of the tobacco tar cavity is sealed by a first seal seat, a groove is formed in a middle of the first seal seat, and a first tobacco tar isolation seat is mounted in the groove;

wherein the first tobacco tar isolation seat is T-shaped and comprises a first vertical portion and a first flange edge at a top of the first vertical portion, the first vertical portion is inserted into the groove, a first gap is reserved between the first vertical portion and an inner wall of the groove, the first gap is filled with a tobacco tar storage cotton, and the first flange edge is provided with a first tobacco tar pass hole, which communicates with the tobacco tar cavity, in a position corresponding to the tobacco tar storage cotton;

and wherein the atomizing cotton is wrapped on an outer wall of the first vertical portion, and an outer side of the atomizing cotton abuts against the tobacco tar storage cotton; and the base body is fixedly connected with the first vertical portion.

5. The atomizer according to claim 3, wherein a first seal cover that is open at a bottom is arranged at the lower part of the base body, a second seal cover that is open at a bottom is arranged in an inner cavity of the first seal cover, a gap is reserved between the first seal cover and the second seal cover, and an inner cavity of the second seal cover communicates with the hollow cavity of the base body;

wherein the first seal cover is provided with a first air guide groove in a position corresponding to the first air pass hole, and the second seal cover is provided with a second air guide groove in a position corresponding to the first air guide groove;

wherein the air guide passage is formed among the first air guide groove, the second air guide groove, and the gap between the first seal cover and the second seal cover;

and wherein the first seal cover and the second seal cover abut against the atomizing cotton.

6. The atomizer according to claim 3, wherein the hollow cavity of the base body directly reaches a bottom of the base body, a cover which blocks the hollow cavity of the base body is arranged at the bottom of the base body, the cover is provided with a second air pass hole in a position corresponding to the first air pass hole, and the second air pass hole is the air guide passage;

wherein a bottom of the cover abuts against the atomizing cotton, and a third air pass hole is formed at the abutting position.

7. The atomizer according to claim 6, wherein the cover is spherical or inversely conical.

8. The atomizer according to claim 2, wherein the air inlet is provided at an upper part of the shell, an accommodating cavity is formed in the middle of the tobacco tar cavity, the air outflow pipe is arranged in the accommodating cavity, a first gap (A) is reserved between an outer wall of the air outflow pipe and an inner wall of the accommodating cavity, and the first gap (A) communicates with the air inlet to form the first air inflow passage;

wherein a flange is arranged at the lower part of the air outflow pipe near an orifice of the air outflow pipe, the air guide structure comprises a flexible tube sleeved at the orifice of the air outflow pipe below the flange, a lower part of the flexible tube is provided with an air pass groove, and a bottom of the flexible tube abuts against a bottom of the hollow cavity of the atomizing cotton;

wherein after the air outflow pipe is inserted into the hollow cavity of the atomizing cotton, an upper surface of the flange is directly opposite to an outlet of the first air inflow passage; a second gap (E) is reserved between the flange and the outlet of the first air inflow passage, and a side of the flange is close to an inner wall of the hollow cavity of the atomizing cotton, and a third gap is reserved between the flange and the inner wall of the hollow cavity of the atomizing cotton.

9. The atomizer according to claim 8, wherein a bottom of the tobacco tar cavity is sealed by a seal seat, a groove is formed in a middle of the seal seat, and a tobacco tar isolation seat is mounted in the groove;

wherein the tobacco tar isolation seat is T-shaped and comprises a vertical portion and a flange edge at a top of the vertical portion, the vertical portion is inserted into the groove, a fourth gap is reserved between the vertical portion and an inner wall of the groove, the fourth gap is filled with a tobacco tar storage cotton, and the flange edge is provided with a tobacco tar pass hole, which communicates with the tobacco tar cavity, in a position, corresponding to the tobacco tar storage cotton;

and wherein a side of the atomizing cotton is wrapped on an outer wall of the vertical portion, and the side of the atomizing cotton abuts against the tobacco tar storage cotton.

10. The atomizer according to claim 9, wherein a bottom of the atomizing cotton is provided with a first air outlet.

11. The atomizer according to claim 10, wherein a lower part of the vertical portion is sleeved with a spring, the spring is wrapped by the atomizing cotton, a lower end of the spring abuts against an inner surface of the bottom of the atomizing cotton, the lower part of the air outflow pipe penetrates through the tobacco tar isolation seat and is inserted into the central hole of the spring, and the flexible tube communicates with the first air outlet.

12. The atomizer according to claim 9, wherein the flexible tube is a glass fiber tube, and comprises a first glass fiber tube sleeved at the lower part of the air outflow pipe and a second glass fiber tube sleeved at an upper part of an outer wall of the first glass fiber tube;

wherein a length of the second glass fiber tube is shorter than that of the first glass fiber tube, and the air pass groove is formed at a lower part edge of the first glass fiber tube.

13. The atomizer according to claim 8, wherein a filter screen is arranged at a lower part of the air outflow pipe.

14. The atomizer according to claim 2, wherein the air inlet is provided at an upper part of the shell, a tobacco tar isolation cavity is formed in a middle of the tobacco tar cavity, an accommodating cavity is formed in the tobacco tar isolation cavity, the air outflow pipe is arranged in the accommodating cavity, a gap (B) is reserved between an outer wall of the air outflow pipe and an inner wall of the accommodating cavity, and the gap (B) communicates with the air inlet to form the first air inflow passage;

wherein the air guide structure comprises a liner tube which is sleeved in the air outflow pipe and has a performance of thermal insulation and tobacco tar absorption, a gap (C) is reserved between a lower end of the air outflow pipe and a bottom of the hollow cavity of the atomizing cotton, a lower end of the liner tube stretches out of the lower end of the air outflow pipe and abuts against the bottom of the hollow cavity of the atomizing cotton, a lower part edge of the liner tube is provided with an air pass hole (F) which communicates with the first air inflow passage, and the air pass hole (F) is the air guide passage.

15. The atomizer according to claim 14, wherein a height of the air pass hole F is 0.2 to 0.7 mm.

16. The atomizer according to claim 14, wherein the accommodating cavity is composed of an outer sleeve and an inner sleeve sleeved in an inner cavity of the outer sleeve, the outer sleeve comprises a hollow seal seat arranged at a bottom of the tobacco tar cavity to seal the tobacco tar cavity and a vertical pipe fixed on the seal seat, the inner sleeve is sleeved in an inner cavity of the vertical pipe, and an inner cavity of the inner sleeve is the accommodating cavity;

wherein an atomizing sheet fixing holder is arranged in a hollow cavity of the seal seat, and the atomizing sheet is fixed on the atomizing sheet fixing holder;

wherein a side wall of the atomizing cotton is sandwiched and fixed between an outer wall of the inner sleeve and an inner wall of the vertical pipe; a lower part of the vertical pipe is provided with a plurality of tobacco tar pass holes in positions corresponding to the side wall of the atomizing cotton, and the tobacco tar pass holes communicate with the tobacco tar cavity;

and wherein the air outflow pipe with the liner tube is inserted into a hollow cavity of the inner sleeve as well as the hollow cavity of the atomizing cotton.

17. The atomizer according to claim 16, wherein a tobacco tar storage cotton is sleeved on an outer wall of the vertical pipe at a position corresponding to the tobacco tar pass holes, and the tobacco tar storage cotton is located in the tobacco tar cavity and covers the tobacco tar pass holes.

18. The atomizer according to claim 16, wherein a lower part of the inner cavity of the inner sleeve is sleeved with a spring, a lower end of the spring abuts against an inner surface of the bottom of the atomizing cotton, and the air outflow pipe with the liner tube is inserted into the hollow cavity of the inner sleeve as well as a central hole of the spring.

19. The atomizer according to claim 14, wherein the air outflow pipe is flush with an upper end of the liner tube, and a filter screen is arranged at the upper part of the liner tube.

20. The atomizer according to claim 14, wherein the liner tube is a glass fiber tube, and the air pass hole F is zigzag groove or wave groove formed around a lower part edge of the liner tube.

21. The atomizer according to claim 14, wherein a height of the gap C between the air outflow pipe and the bottom of the hollow cavity of the atomizing cotton is more than 2 mm.

22. The atomizer according to claim 14, wherein the upper end of the liner tube extends out of an upper end of the air outflow pipe and extends into an inner cavity of the suction nozzle assembly, and a gap (D) is reserved between an outer wall of the liner tube and an inner cavity wall of the suction nozzle assembly;

wherein the suction nozzle assembly is detachably connected to the top of the shell.

23. The atomizer according to claim 14, wherein a thermal insulation sheet is arranged between a lower surface of the atomizing sheet and the connection electrode.

* * * * *